United States Patent [19]

Wallack

[11] 4,108,983

[45] Aug. 22, 1978

[54] VIRAL ONCOLYSATE VACCINE FOR STIMULATING THE IMMUNE MECHANISM OF MAMMALS TO SPECIES-SPECIFIC TUMORS

[75] Inventor: Marc K. Wallack, Cherry Hill, N.J.

[73] Assignee: The Wistar Institute, Philadelphia, Pa.

[21] Appl. No.: 691,486

[22] Filed: Jun. 1, 1976

[51] Int. Cl.² .................. A61K 39/12; C12K 9/00
[52] U.S. Cl. ............................ 424/89; 195/1.8
[58] Field of Search .......................... 195/1.8; 424/89

[56] References Cited

U.S. PATENT DOCUMENTS 3,553,312  1/1971  Delgado ........................... 195/1.8

Primary Examiner—Sam Rosen

[57] ABSTRACT

A virus-lysed tumor cell vaccine is an active immunotherapeutic agent against tumors in mammals. In particular, a vaccine based upon vaccinia virus-lysed, species-specific tumor cells is an effective stimulator of the immune response in mammals, and a vaccine based upon vaccinia virus-lysed spontaneously arising tumor cells is an effective stimulator of the immune response in some human cancer patients. A process for preparing the vaccine by viral oncolysis is also disclosed. Tumor cells are removed from a mammal, the cells are cultured in a culture medium and infected with live vaccinia virus. Viral oncolysis occurs during incubation and the resulting viral oncolysate, after extraction, may be injected into mammals to stimulate the immune response mechanism.

17 Claims, No Drawings

VIRAL ONCOLYSATE VACCINE FOR STIMULATING THE IMMUNE MECHANISM OF MAMMALS TO SPECIES-SPECIFIC TUMORS

BACKGROUND OF THE INVENTION

This invention relates to a vaccine capable of stimulating the immune response of a tumorous mammal against mammalian tumors, and, in particular, against species-specific mammalian tumors. Species-specific tumors are those which are specific to a particular species of mammal. The tumors may be induced, as can be the BALB/C male mouse peritoneal macrophage tumor, designated $GMMSVI_2$, or may arise spontaneously as does colon cancer in humans.

The phenomenon of viral oncolysis or the lysis of tumor cells by viruses with its resultant post-viral oncolytic immunity has been a subject of cancer research for approximately thirty years. One of the most notable contributions to this field is the work of J. Lindenmann entitled "Viruses as Immunological Adjuvants in Cancer", which appeared in *Biochimica et Biophysica Acta*, 355 (1974) 49–75. This article details the history of viral oncolysis from its inception in 1929 to 1974. Lindenmann has also reported that influenza A virus is capable of lysing transplanted Ehrlich Ascites cells in the peritoneal cavities of $A_2G$ mice when injected directly into the tumor filled peritoneal cavity. The mice surviving the influenza oncolysis were noted to have developed post-viral oncolytic immunity and resisted rechallenge with the same tumor. Lindenmann, "Immunity to Transplantable Tumors Following Viral Oncolysis," *J. Immunology*, Vol. 92, pp. 912–919 (1964).

Asada injected mumps virus directly into tumors of patients with various kinds of terminal cancer and 25% of the patients showed some suppressed tumor growth, Asada, T., "Treatment of Human Cancer with Mumps Virus", *Cancer*, 34 (1907, 1974). Numerous other viruses have been injected into mammals bearing tumors to effect in vivo viral oncolysis. Among the viruses worked with are vesicular stomatitis virus, reovirus, mumps virus and West Nile virus. This technique, though promising, is difficult to apply in practice since most oncolytic viruses described in the art are harmful to man, and attempts to directly infect "in vivo" human tumor cells have yielded unsatisfactory results.

Attempts have also been made to stimulate the immune response of mammals to nonspecies-specific, transplantable tumors such as Ehrlich Ascites by preparing an in vitro viral oncolysate of influenza A or vesicular stomatitis virus prepared in suspension culture of Ehrlich Ascites cells. Mice immunized with the Ehrlich Ascites viral oncolysate were resistant to intraperitoneal challenge with living Ehrlich Ascites cells. Hakkinen et al., "Induction of Tumor Immunity in Mice with Antigen Prepared From Influenza and Vesicular Stomatitis Virus Grown in Suspension Culture of Ehrlich Ascites Cells", *Journal of the National Cancer Institute*, Vol. 46, No. 6, June 1971.

Bandlow et al have noted that vaccinia virus acts as an immunological adjuvant in the production of heterologous cytotoxic antibodies against host cell antigens and that guinea pigs show an increased cell-mediated immunity against host cell antigens after active immunization with vaccinia virus infected tissue culture cells. See Bandlow et al. "Untersuchungen zum Mechanismus der immunologischen Adjuvanswirkung des Vacciniavirus", *Archiv fur die gesamte Virusforschung* 38, 192–204 (1972) and "Increased Cellular Immunity Against Host Cell Antigens Induced by Vacciniavirus", *Archiv fur die gesamte Virusforschung* 45, 122–127 (1974).

DESCRIPTION OF THE INVENTION

It is an object of this invention to provide a virus-lysed species-specific tumor cell vaccine (viral oncolysate) for mammals which is an active immunotherapeutic agent against species-specific mammalian tumors and which has no harmful effect on the mammal.

It is a further object of this invention to provide a virus-lysed tumor vaccine (viral oncolysate) which is an active immunotherapeutic agent against some human tumors in some patients.

It is still further an object of this invention to provide a process for preparing a viral oncolysate vaccine for species-specific tumor cells.

It is yet another object of this invention to provide a process of treating a tumorous human patient with a viral oncolysate vaccine specific for tumors, which vaccine is less pathogenic for humans than is the tumor.

It is also an object of this invention to provide a vaccine which is a viral oncolysate of a patient's autochthonous tumor which vaccine can be used to stimulate the immune mechanism of some patients against the patient's autochthonous tumor.

It is still further an object of this invention to provide a vaccine which is a viral oncolysate of a species-specific tumor, especially a spontaneous malignant tumor, which vaccine can be used to stimulate the immune mechanism of other patients of the same species afflicted or potentially afflicted by the same type of tumor.

These and other objects of this invention can be achieved by a vaccine for stimulating the immune mechanism of mammals to species-specific tumors which comprises a viral oncolysate of said tumor and a virus having a lytic action on the cells of said tumor, said virus being substantially less pathogenic for said mammal than is said tumor, and said viral oncolysate being the product of an in vitro oncolysis reaction.

In another aspect of this invention, I have achieved these objectives by a vaccine for stimulating the immune mechanism of mammals to species-specific tumors prepared by removing tumor tissue from a mammal and growing cells of said tumor in a culture medium, infecting said cells with a virus capable of lysing said cells, said virus being less pathogenic for said mammal than is said tumor, and culturing said cells and virus until oncolysis occurs.

In yet another aspect of this invention, I have developed a method of forming and using a vaccine capable of stimulating the immune mechanism of mammals to species-specific tumors, especially spontaneous malignant tumors, comprising infecting cells of the tumor in vitro with a virus which is substantially less pathogenic for said mammal than is said tumor, maintaining said virus infected cells under culture conditions until a viral oncolysate is formed, harvesting said oncolysate and administering said oncolysate to said mammal.

It is essential that the virus from which the oncolysate is formed be less pathogenic to the mammal than the tumor since little is gained if the mammal contracts the virion associated disease and succumbs to the disease. It is also necessary that the virus have a lytic action on tumor cells especially human tumor cells. In this regard, I have tested in vitro the vaccine strengths of six viral vaccines (measles, mumps, rubella, yellow fever, rabies, and vaccinia) against four human tumor lines, melanoma, lung, pharynx and ovary, and found that only vaccinia vaccine had a lytic action on the human tumors of the same sort as does the influenza virus on Ehrlich Ascites cells. Moreover, because the safety of both lysed tumor cell vaccines and the vaccinia vaccine itself have been previously established for man, an oncolysate prepared from vaccinia lysed tumor cells is not harmful. Surprisingly, although the vast majority of humans have been previously innoculated with vaccinia as a prevention against smallpox, the previous innoculation appears to have no effect on the efficacy of the vaccine.

Although I have selected vaccinia virus as the virus to be used for preparing the viral oncolysate, my invention is not to be limited solely to the use of vaccinia virus, since any other live virus vaccine may be used so long as the virus is capable of lysing the tumor cells and is less pathogenic for the mammal into which the viral oncolysate is to be injected than the tumor cells themselves.

It is currently accepted theory that all tumor cells of a particular variety are characterized by a common tumor antigen usually located at the tumor cell surface. As a species-specific tumor grows in its specific host species, the immune mechanism of the host is somehow suppressed or made ineffective. When, however, species-specific tumor cells are lysed by the live vaccinia virus, the antigen of the virus and the antigen of the tumor combine to form a neo-antigen which when injected into a patient serves to stimulate the immune mechanism of the patient to the neo-antigen and to the antigen of tumor. This surprisingly occurs even when the host is preimmunized with vaccinia vaccine. Because tumor antigens are common to particular varieties of tumors, the vaccine is effective against tumors bearing the same antigen in the same species of mammal regardless of the particular host from which the initial tumor was obtained.

I contemplate the maintenance of large volume laboratory tissue cultures of species-specific or autochthonous tumors of varieties of tumors such as hepatoma cells, colon cancer cells, etc. Cells can be taken from these laboratory cultures for the preparation of fresh vaccine. The vaccine could be administered to patients whose tumors are inaccessible by standard surgical techniques. Alternatively, vaccine prepared from tumor cells obtained from one patient may be used to stimulate the immune mechanism of other patients having the same variety of tumor.

Experiments with mice have confirmed the safety and efficacy of the vaccine against species-specific tumors in animal models. In my experiments, there was no vaccine associated deaths and, furthermore, tumors failed to grow in animals prevaccinated with the vaccinia oncolysate.

Vaccine Preparation

The vaccinia oncolysate may be prepared by infecting monolayers of tumor cells with 1 ml of live vaccinia virus and incubating for 96 hours. The oncolysate is then frozen and thawed three times and harvested by centrifugation of the lysed cellular debris at 39,100 g for 45 minutes at 0° C. The supernatent is removed and the pellet is resuspended in saline solution and homogenized to accomplish further cell destruction. The lysate is again centrifuged at 39,100 g and concentrated to effect a concentration of $1 \times 10^6$ vaccinia-lysed tumor cells per ml. This final concentrate constitutes a vaccinia oncolysate vaccine.

Alternative to the infection of monolayers, it is highly preferable and constitutes at least a part of this invention that the tumor cells be infected with the vaccinia virus while the tumor cells are in suspension because of the ease of keeping human tumor cells alive for short periods of time in suspension. The advantage of suspension culture is that the tumor used to prepare the viral vaccine may be difficult to grow in monolayer culture but easily grown for short periods in suspension. When tumor cells taken from a patient are maintained in suspension, they may be easily infected with vaccinia virus and the oncolysate vaccine may be rapidly prepared and reinjected into the same patient or a different patient with the same type of tumor, i.e., colon cancer, gastric cancer, breast cancer, etc.

1. Animal Experiments a. Animals

All experiments were conducted in BALB/C male mice, 8-10 weeks old at the time of implantation of the tumor isografts. Each treatment and control group consisted of 6-8 mice, randomly distributed.

b. Tumor Cells

An SV40-transformed BALB/C male mouse peritoneal macrophage tumor, designated GMMSVI$_2$, was used in all experiments. Tumor cells in doses ranging from $1 \times 10^3$ to $1 \times 10^5$ cells were injected subcutaneously into the left thigh of the mice.

c. Virus

A standard vaccinia virus vaccine was obtained and cultured on WI-38 cells under standard conditions to increase the titer of the vaccine. Vaccine titers were determined on monolayers of WI-38 cells in Eagle's minimal essential medium (MEM), containing 3% fetal bovine serum (FBS). The vaccinia titer was increased to approximately $1 \times 10^8$ TCID$_{50}$/ml. When the experiments called for prevaccination with vaccinia virus prior to vaccination with the vaccinia oncolysate, the virus was diluted 1:1000 in phosphate buffered saline (PBS) before injection.

d. Vaccine Preparation

The vaccinia oncolysate was prepared by infecting monolayers of $1 \times 10^6$ GMMSVI$_2$ tumor cells with 1 ml of vaccinia virus ($1 \times 10^8$ TCID$_{50}$/ml) and incubating for 96 hours. The oncolysate was then frozen and thawed three times and harvested by centrifugation of the lysed cellular debris at 39,100 g for 45 minutes at 0° C. The pellet was then resuspended in 10 ml of Eagle's MEM without FBS and further cell destruction accomplished by using a Dounce homogenizer. This lysate was again centrifuged at 39,100 g and suspended in enough Eagle's MEM without FBS so as to effect a concentration of $1 \times 10^6$ vaccinia-lysed tumor cells per ml. This final concentration was the vaccinia oncolysate used in all the animal experiments. The vaccinia oncolysate was always injected subcutaneously into the right thigh. The quantity and the number of treatments are described hereinafter.

e. Results

Groups of 6-8 mice were injected subcutaneously into the right thigh with 0.3 ml of vaccinia oncolysate on day $-17$, $-12$, $-7$, $-3$, 0 and then received either $1 \times 10^3$, $1 \times 10^4$ or $1 \times 10^5$ tumor cells subcutaneously into the left thigh on day 0. The mice were followed for approximately 60 days.

Mice prevaccinated with the vaccinia oncolysate prior to receiving tumor cells failed to develop tumors at the injection site as compared to controls.

Moreover, 6 mice which were preimmunized with 0.3 ml of vaccinia virus (diluted with PBS to $1 \times 10^5$ $TCID_{50}$/ml) subcutaneously into the right thigh and then immunized $1 \times 10^4$ tumor cells also failed to develop tumors as compared to controls.

2. Human Experiments a. Humans

The following cancer patients were selected for treatment with the vaccinia oncolysate (vaccinia-lysed spontaneous tumor cell vaccine): (1) Cancer patients who had tumor resections and showed tumor metastasis to local and/or regional lymph nodes; (2) Patients submitted to radiation therapy for localized, unresectable disease; (3) Patients with disseminated disease treated by chemotherapy but considered terminal; (4) Patients with disease so far advanced that they were deemed untreatable by surgery, chemotherapy, or radiotherapy. All patients involved in these therapeutic trails gave informed consent by signing an authorization for the use of investigational therapy and showed a delayed hypersensitivity response to one of the common recall antigen skin tests used to gauge immunocompetence. An essential requirement was that cells from a tumor could be surgically obtained and grown in tissue culture, either in suspension or monolayer.

b. Vaccine Preparation

Tumor tissue removed from the patient in the operating room was processed as follows: (1) Those portions of the tumor that are not necrotic, fatty or hemorrhagic are finely minced by scalpels and placed in Eagle's MEM with 20% FBS (fetal bovine serum) plus penicillin and gentamicin; (2) The minced tissue is placed in an Erlenmeyer flask with 30 ml of 0.25% trypsin 1% versene solution and stirred with a magnetic bar to effect a suspension of single cells; (3) Approximately $1 \times 10^8$ $TCID_{50}$/ml of live vaccinia virus is used to infect $1 \times 10^6$/ml of tumor cells in suspension; (4) The virus-tumor cell suspension is incubated for 96 hours at 37° C. in Spinner's medium while both tumor cell lysis and virus titer were monitored; (5) The vaccinia virus-lysed tumor cell suspension is spun at 39,100 g for 60 minutes at 0° C., the supernatant removed and the resulting pellet suspended in 10 ml of Eagle's MEM as the harvested oncolysate. The oncolysate is then collected in a sterile homogenizer tube, Dounce homogenized 20 times, centrifuged at 39,100 g for 60 minutes at 0° C., and the pellet resuspended in enough Eagle's MEM to effect a concentration of $1 \times 10^6$ vaccinia-lysed tumor cells per ml. These 1 ml aliquots will be frozen at 0° C. for use later. The vaccine may be stored at $-70°$ C. $\pm$ 10° C. for up to two years.

c. Vaccine Administration

The vaccinia oncolysate vaccine having a concentration of $1 \times 10^6$ vaccinia-lysed tumor cells per ml was injected in 1 ml doses. Each dose was divided and injected intradermally into the anterior thigh, upper arm and anterior thorax to stimulate regional lymph nodes. The oncolysate injections were given every two weeks for three months.

d. Patient Monitoring

The following laboratory studies were done every four weeks during the course of immunotherapy: (a) CBC; (b) BUN; (c) glucose; (d) SGPT; (e) SGOT; (f) LDH; (g) bilirubin; (h) alkaline phosphatoase; (i) quantative immunoglobulins; (j) PHA-induced blastogenesis; (k) lymphocyte cytotoxicity; (l) vaccinia antibody titer; and (m) anergy panel and DNCB.

e. Results

A total of 13 tumor patients received the full course of vaccinia oncolysate immunotherapy. These patients represent four cases of colon carcinoma, two cases of gastric carcinoma, three cases of melanoma, two cases of ovarian carcinoma, one case of pharyngeal carcinoma and one case of thyroid carcinoma.

Patient response to the vaccinia oncolysate immunotherapy was as follows: (1) 0/13 patients had adverse reactions; (2) 6/13 patients died; (3) 6/7 patients surviving had delayed hypersensitivity reactions at the vaccine injection sites; (4) 6/6 patients with positive skin reactions to the vaccine had elevated antibody titers; (5) 6/6 patients with positive skin reactions to the vaccine had previous positive reactions to common recall antigens; (6) 6/6 patients with positive skin reactions to the vaccine showed positive lymphocyte transformation to PHA; (7) 2/6 patients with positive skin reactions to the vaccine had reduction in tumor burden after immunotherapy.

Case Reports of the Two Responders (1) Case 1

A 61-year old female had a level III malignant melanoma metastatic from the back to the left axilla and liver with resultant hepatomegaly and abnormal liver function studies. The patient received six 1 ml dose treatments of the vaccinia oncolysate at two-week intervals. Each dose was divided and injected intradermally into the upper arms, anterior thorax and thighs and developed massive delayed hypersensitivity response at these sites. The patient now has a normal liver scan, no hepatomegaly, normal liver function studies and no evidence of new metastatic disease.

(2) Case 2

D. J. is a 46-year old woman who had an abdominal-perineal resection for Dukes B colon cancer. The patient developed a massive local perineal tumor recurrence that was refractory to radiotherapy. She then received four 1 ml dose treatments of the vaccinia oncolysate at two-week intervals. Each dose was divided and injected in proximity to regional lymph nodes with two injections being directly into the perineal tumor mass. The patient developed a significant delayed hypersensitivity response at the tumor site after the intratumor injections and subsequently there was a 50% reduction in the size of the tumor.

I claim:

1. A method of forming a vaccine capable of stimulating the immune mechanism of mammals to species-specific tumors comprising infecting cells of a species-specific tumor in vitro with a virus having a lytic action on the cells of said tumor, said virus comprising vaccinia virus and being substantially less pathogenic for said mammal than is said tumor, maintaining said virus infected cells under culture conditions until a viral oncolysate is formed and harvesting said oncolysate.

2. The method of claim 1 wherein said tumor is a spontaneous malignant tumor.

3. The method of claim 1 wherein said mammal is man.

4. The method of claim 1 wherein said virus infected cells are maintained in suspension culture.

5. The method of claim 2 wherein said virus infected cells are maintained in suspension culture.

6. A vaccine for stimulating the immune mechanism of mammals to species-specific tumors, said vaccine comprising the viral oncolysate of a species-specific tumor and a virus having a lytic action on the cells of said tumor, said virus comprising vaccinia virus and being substantially less pathogenic for said mammal than is said tumor, said viral oncolysate being the product of an in vitro oncolysis reaction.

7. The vaccine of claim 6 wherein said mammal is man.

8. The vaccine of claim 6 prepared in vitro in suspension culture of said tumor cells.

9. The vaccine of claim 6 wherein said tumor is a spontaneous malignant tumor.

10. The vaccine of claim 7 prepared in vitro in suspension culture of said tumor cells.

11. A method of stimulating the immune mechanism of mammals to species-specific tumors comprising removing tumor tissue from a species of said mammal and growing tumor cells of said tissue in a culture medium, infecting said cells with a virus capable of lysing said cells, said virus comprising vaccinia virus and being less pathogenic for said mammal than is said tumor, culturing said cells and virus until oncolysis occurs and injecting the viral oncolysate into a mammal of the same species.

12. The method of claim 11 wherein said tumor cells are suspended in said culture medium.

13. The method of claim 11 wherein said mammal is human.

14. The method of claim 12 wherein said mammal is human.

15. The method of claim 11 wherein said mammal into which the viral oncolysate is injected bears a tumor of the same variety from which the oncolysate is prepared.

16. The method of claim 15 wherein said tumor tissue removed is an autochthonous tumor and said viral oncolysate is injected into the same mammal from which said tumor tissue is obtained.

17. The method of claim 16 wherein said mammal is human.

* * * * *

UNITED STATES PATENT AND TRADEMARK OFFICE
CERTIFICATE OF CORRECTION

PATENT NO. : 4,108,983
DATED : August 22, 1978
INVENTOR(S) : Marc K. Wallack

It is certified that error appears in the above—identified patent and that said Letters Patent is hereby corrected as shown below:

Column 1, immediately below the Title, add the following

-- The invention described herein was made in the course of work under a grant or award from The Department of Health, Education and Welfare --

Signed and Sealed this

Twenty-first Day of October 1980

[SEAL]

Attest:

SIDNEY A. DIAMOND

Attesting Officer

Commissioner of Patents and Trademarks